United States Patent
Jamison et al.

(10) Patent No.: US 11,029,246 B1
(45) Date of Patent: Jun. 8, 2021

(54) COLORIMETRIC DETECTION OF SHALE INHIBITORS AND/OR SALTS

(71) Applicant: Halliburton Energy Services, Inc., Houston, TX (US)

(72) Inventors: Dale E. Jamison, Humble, TX (US); Xiangnan Ye, Cypress, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 17/110,717

(22) Filed: Dec. 3, 2020

Related U.S. Application Data

(60) Provisional application No. 62/992,619, filed on Mar. 20, 2020.

(51) Int. Cl.
| | | |
|---|---|---|
| *G01N 21/25* | (2006.01) | |
| *G01N 1/38* | (2006.01) | |
| *G01N 31/22* | (2006.01) | |
| *G01N 33/28* | (2006.01) | |

(52) U.S. Cl.
CPC ............ *G01N 21/25* (2013.01); *G01N 1/38* (2013.01); *G01N 31/22* (2013.01); *G01N 33/2823* (2013.01)

(58) Field of Classification Search
CPC .......... G01N 21/25; G01N 1/38; G01N 31/22; G01N 33/2823
See application file for complete search history.

(56) References Cited

U.S. PATENT DOCUMENTS

| | | |
|---|---|---|
| 7,022,517 B1 | 4/2006 | McDevitt et al. |
| 8,361,804 B2 | 1/2013 | Horton et al. |
| 8,379,207 B2 | 2/2013 | DiFoggio et al. |
| 8,575,541 B1* | 11/2013 | Jamison ............... G01N 21/85 250/253 |
| 2004/0098202 A1 | 5/2004 | McNeil, III et al. |

(Continued)

OTHER PUBLICATIONS

Hang, Pham Thi et al., "Methylene Blue Absorption by Clay Minerals. Determination of Surface Areas and Cation Exchange Capacities (Clay-Organic Studies XVIII," Clays and Clay Minerals, 1970, pp. 203-212, vol. 18, Pergamon Dress.

(Continued)

*Primary Examiner* — Jamil Ahmed
(74) *Attorney, Agent, or Firm* — Conley Rose, P.C.; Rodney B. Carroll

(57) ABSTRACT

A method of detecting a shale inhibitor and/or a salt content in a wellbore servicing fluid (WSF), the method comprising determining a water salinity of a wellbore servicing fluid; dosing a known volume of the wellbore servicing fluid into a container; optionally adding a known volume of diluent (e.g., water) and mixing to provide a test sample; combining the test sample with a chromophore specific to the shale inhibitor and/or the salt, respectively, and optionally mixing; measuring the shale inhibitor content and/or the salt content, respectively, of the test sample using colorimetry; reporting the data from the measuring to a computer control system; determining a wellbore servicing fluid treatment based on the measured shale inhibitor content and/or salt content; subjecting the wellbore servicing fluid system to the treatment; and optionally waiting for a waiting time to retest the wellbore servicing fluid system and repeating.

20 Claims, 2 Drawing Sheets

FIG. 1

(56) References Cited

U.S. PATENT DOCUMENTS

| | | |
|---|---|---|
| 2010/0055800 A1 | 3/2010 | Akhavan-Tafti et al. |
| 2012/0145376 A1 | 6/2012 | Abad et al. |
| 2015/0330215 A1 | 11/2015 | Jamison et al. |
| 2018/0172661 A1* | 6/2018 | Spengler ............ G01N 21/3577 |
| 2019/0119563 A1 | 4/2019 | He et al. |

OTHER PUBLICATIONS

Kostesha, N.V. et al., "Development of the colorimetric sensor array for detection of explosives and volatile organic compounds in air," Technical University of Denmark, 9 pages.

Filing Receipt, Specification and Drawings for U.S. Appl. No. 62/992,619, entitled "Colorimetric Detection of Shale Inhibitors and/or Salts," filed Mar. 20, 2020, 40 pages.

Foreign Communication of Related Application—International Search Report and Written Opinion of the International Searching Authority, International Application No. PCT/US2020/063898, dated Mar. 16, 2021, 11 pages.

\* cited by examiner

COLORIMETRIC DETECTION OF SHALE INHIBITORS AND/OR SALTS

CROSS-REFERENCE TO RELATED APPLICATIONS

This application claims priority under 35 U.S.C. § 119(e) to U.S. Provisional Patent Application No. 62/992,619 filed on Mar. 20, 2020 and entitled "Colorimetric Detection of Shale Inhibitors and/or Salts," the disclosure of which is hereby incorporated herein by reference in its entirety.

BACKGROUND

This disclosure relates to methods of servicing a wellbore. More specifically, it relates to methods of detecting shale inhibitors and/or salts in wellbore servicing fluids.

Natural resources such as gas, oil, and water residing in a subterranean formation or zone are usually recovered by drilling a wellbore down to the subterranean formation while circulating a drilling fluid in the wellbore. After terminating the circulation of the drilling fluid, a string of pipe, e.g., casing, is run in the wellbore. The drilling fluid is then usually circulated downward through the interior of the pipe and upward through the annulus, which is located between the exterior of the pipe and the walls of the wellbore. Shale inhibitors and salts are ubiquitous components in drilling fluids. Shale inhibitors and/or salts can have predetermined concentrations in drilling fluids to prevent problems during the drilling process, such as viscosity build-up, bit balling, wellbore caving and ballooning, etc. However, during the drilling process, shale inhibitors and/or salts can be lost to or gained from the formation. The inability to accurately identify the active concentration of shale inhibitors and/or salts in drilling fluids in real-time can result in economic losses (e.g., increased incidence of non-productive time). Thus, an ongoing need exists for real-time quantitative detection of shale inhibitors and/or salts in wellbore servicing fluids, such as drilling fluids.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
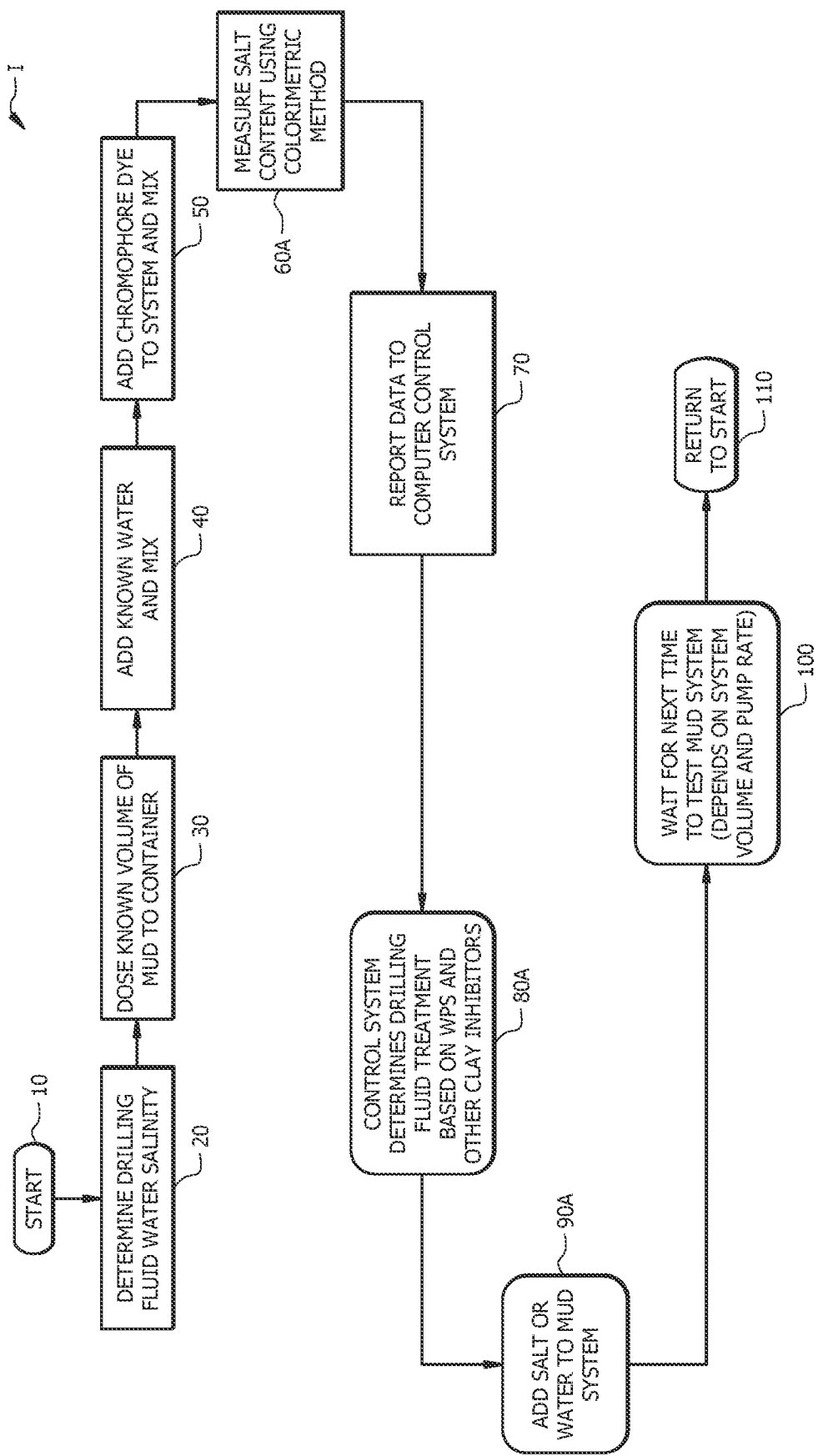
FIG. 1 is a flow chart showing a representative method for measuring a salt content in a wellbore servicing fluid according to this disclosure.

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques below, including the exemplary designs and implementations illustrated and described herein, but may be modified within the scope of the appended claims along with their full scope of equivalents.

Disclosed herein are methods of detecting shale inhibitors and/or salts in wellbore servicing fluids or compositions (collectively referred to herein as WSFs). The amount (e.g., concentration) of shale inhibitors and/or salts can be determined by reacting the shale inhibitors and/or salts with a detector compound, which may result in highly conjugated molecules that display color (e.g., visual color); wherein such highly conjugated molecules can absorb light in the ultraviolet-visible (UV-VIS) range and/or in the visible (VIS) range; and wherein the absorption intensity can be used to derive the amount of the shale inhibitors and/or salts in the WSF. Although described hereinbelow with reference to absorbance, in aspects light reflectance can be utilized.

In an aspect, a method of detecting a shale inhibitor and/or a salt in a WSF can include (a) contacting an aliquot of the WSF with a detector compound to form a detection solution; wherein the WSF includes the shale inhibitor and/or the salt; and wherein the detection solution is characterized by at least one absorption peak wavelength in the range of from about 380 nanometers (nm) to about 760 nm; (b) detecting an absorption intensity for the detection solution at a wavelength within about ±20% of the at least one absorption peak wavelength; (c) comparing the absorption intensity of the detection solution at the wavelength within about ±20% of the at least one absorption peak wavelength with a target absorption intensity of the shale inhibitor and/or the salt to determine the amount of the shale inhibitor and/or the salt in the WSF; and (d) comparing the amount of the shale inhibitor and/or salt in the WSF with a target amount of the shale inhibitor and/or the salt. The detection solution can be characterized by a visible color. In some aspects, the aliquot of the WSF can be further characterized by a visible color, wherein the visible color and/or color intensity of the detection solution is different from the visible color and/or color intensity of the aliquot of the WSF. In other aspects, the aliquot of the WSF can be colorless, for example the aliquot of the WSF can be a clear liquid.

Further disclosed herein are methods of servicing a wellbore in a subterranean formation including the real-time detection of shale inhibitors and/or salts in WSF used in the wellbore and/or subterranean formation.

In an aspect, a method of servicing a wellbore in a subterranean formation can include preparing a WSF including a base fluid and a shale inhibitor and/or salt, wherein the shale inhibitor and/or salt is present in the WSF in a target amount. The target amount can be greater than or equal to zero. For example, the target amount of the salt may be zero, in aspects.

In an aspect, the WSF suitable for use in the present disclosure may include any suitable WSF. As used herein, a "servicing fluid" or "treatment fluid" refers generally to any fluid that may be used in a subterranean application in conjunction with a desired function and/or for a desired purpose, including but not limited to fluids used to drill, complete, work over, fracture, repair, clean, or in any way prepare a wellbore for the recovery of materials residing in a subterranean formation penetrated by the wellbore. The servicing fluid is for use in a wellbore that penetrates a subterranean formation. It is to be understood that "subterranean formation" encompasses both areas below exposed earth and areas below earth covered by water such as ocean or fresh water. In an aspect, the WSF (e.g., including a base fluid, a shale inhibitor and/or a salt) as disclosed herein can be a drilling fluid or a completion fluid. In an aspect, the WSF as disclosed herein can be a drilling fluid.

In an aspect, the WSF includes a base fluid. In some aspects, the base fluid is an aqueous fluid. In other aspects, the base fluid includes an emulsion.

The salt detected via this disclosure can have monovalent and/or polyvalent cations, alkali and alkaline earth metals, or combinations thereof. Additional examples of suitable salts include NaCl, KCl, NaBr, $CaCl_2$, $CaBr_2$, $MgCl_2$, $MgBr_2$, $ZnBr_2$, acetate salts, sodium acetate, potassium acetate, ammonium chloride ($NH_4Cl$), potassium phosphate, sodium formate, potassium formate, cesium formate, or combinations thereof. In an aspect, the WSF (e.g., the base fluid of the WSF) includes a brine including the salt to be detected.

In an aspect, the base fluid includes an aqueous fluid. Aqueous fluids that may be used in the WSF include any aqueous fluid suitable for use in subterranean applications, provided that the aqueous fluid is compatible with the other components (e.g., shale inhibitor) used in the WSF. For example, the aqueous fluid may include water or a brine. In an aspect, the aqueous fluid includes an aqueous brine. In an aspect, the WSF suitable for use in the present disclosure may include any suitable salt(s). In such aspect, the aqueous brine generally includes water and an inorganic monovalent salt, an inorganic multivalent salt, or both. The aqueous brine may be naturally occurring or artificially-created. Water present in the brine may be from any suitable source, examples of which include, but are not limited to, sea water, tap water, freshwater, water that is potable or non-potable, untreated water, partially treated water, treated water, produced water, city water, well-water, surface water, liquids including water-miscible organic compounds, and combinations thereof. The salt or salts in the water may be present in an amount ranging from greater than about 0% by weight to a saturated salt solution, alternatively from about 1 wt. % to about 30 wt. %, or alternatively from about 5 wt. % to about 10 wt. %, based on the weight of the salt solution. In an aspect, the salt or salts in the water may be present within the base fluid in an amount sufficient to yield a saturated brine. As will be appreciated by one of skill in the art, and with the help of this disclosure, the type and concentration of salt solutions utilized as a base fluid is dependent on the WSF density (e.g., drilling fluid density, completion fluid density, etc.), which may range from about 8 lb/gallon to about 20 lb/gallon, alternatively from about 10 lb/gallon to about 18 lb/gallon, or alternatively from about 12 lb/gallon to about 16 lb/gallon.

Nonlimiting examples of aqueous brines suitable for use in the present disclosure include chloride-based, bromide-based, phosphate-based or formate-based brines containing monovalent and/or polyvalent cations, salts of alkali and alkaline earth metals, or combinations thereof. Additional examples of suitable brines include, but are not limited to brines including salts such as NaCl, KCl, NaBr, $CaCl_2$, $CaBr_2$, $MgCl_2$, $MgBr_2$, $ZnBr_2$, acetate salts, sodium acetate, potassium acetate, ammonium chloride ($NH_4Cl$), potassium phosphate, sodium formate, potassium formate, cesium formate, or combinations thereof. In an aspect, the base fluid includes a brine.

In an aspect, the base fluid includes an emulsion. In such aspect, the emulsion is an oil-in-water emulsion including a non-oleaginous (e.g., an aqueous fluid of the type previously described herein) continuous phase and an oleaginous (e.g., an oil-based fluid, such as for example an oleaginous fluid) discontinuous phase. Oleaginous fluids that may be used in the WSF include any oleaginous fluid suitable for use in subterranean applications, provided that the oleaginous fluid is compatible with the shale inhibitor and/or salt used in the WSF. Examples of oleaginous fluids suitable for use in a WSF include, but are not limited to, petroleum oils, natural oils, synthetically-derived oils, oxygenated fluids, or combinations thereof. In an aspect, the oleaginous fluid includes diesel oil, kerosene oil, mineral oil, synthetic oils, aliphatic hydrocarbons, polyolefins (e.g., alpha olefins, linear alpha olefins and/or internal olefins), paraffins, silicone fluids, polydiorganosiloxanes, oxygenated solvents, esters, diesters of carbonic acid, alcohols, alcohol esters, ethers, ethylene glycol, ethylene glycol monoalkyl ether, ethylene glycol dialkyl ether, or combinations thereof, wherein the alkyl groups are methyl, ethyl, propyl, butyl, and the like.

The base fluid may be present within the WSF in any suitable amount. For example, the base fluid may be present within the WSF in an amount of from about 10 wt. % to about 99 wt. %, alternatively from about 20 wt. % to about 95 wt. %, or alternatively from about 40 wt. % to about 90 wt. %, based on the total weight of the WSF. Alternatively, the base fluid may include the balance of the WSF after considering the amount of the other components used. As will be appreciated by one of skill in the art, and with the help of this disclosure, the amount of base fluid (e.g., aqueous base fluid) in the WSF depends on the desired density of the WSF.

In an aspect, the WSF suitable for use in the present disclosure may include any suitable shale inhibitor.

Shale is a clay-rich sedimentary rock, wherein the shale includes at least about 5 wt. % clay material, based on the total weight of the shale. When shale is exposed to water (e.g., an aqueous fluid; an aqueous-base fluid; a water-containing fluid, such as an emulsion; etc.), the clay in the shale can adsorb water and swell, thereby resulting in potential problems during drilling and/or completion processes, such as viscosity build-up, bit balling, wellbore caving, wellbore ballooning, subterranean formation integrity loss, collapse of subterranean formation, etc.

Generally, a shale inhibitor refers to a chemical compound having the ability to inhibit water-reactive formations (e.g., water-reactive subterranean formations; subterranean formations having water-reactive minerals) from collapsing or losing integrity when the formations come in contact with a water-containing fluid (e.g., an aqueous fluid; an aqueous-base fluid; a water-containing fluid, such as an emulsion; etc.); for example by limiting water uptake by such formations. For purposes of the disclosure herein, the term "water-reactive" refers to formations (e.g., subterranean formations) and/or minerals thereof that can absorb water, uptake water, react with water, and the like, or combinations thereof. Water-reactive formations can encompass any subterranean formations containing clay or clay-based materials, such as shale. For purposes of the disclosure herein, the terms "shale inhibitor" and "clay inhibitor" can be used interchangeably and refer to chemical compounds having the ability to inhibit water uptake by clay-containing subterranean formations (i.e., water-reactive subterranean formations). Without wishing to be limited by theory, clay contains hydrous aluminum silicates having hydroxyl ions that are capable of forming hydrogen bonds. Further, without wishing to be limited by theory, shale inhibitors are chemical compounds having functional groups (e.g., amine functional groups, protonated amine functional groups) that can form hydrogen bonds with the clay (i.e., with the water and/or hydroxyl groups present in the clay), thereby inhibiting water adsorption by the clay material, for example by blocking sites available for hydrogen bonding and rendering such sites unavailable for hydrogen bonding with water molecules. Furthermore, and without wishing to be limited by theory, the shale inhibitor may interact with the subterranean formation via a variety of physical bonds, such as hydrogen bonds, electrostatic interactions, van der Waals interactions, ionic interactions, dipole-dipole interactions, and the like, or combinations thereof.

In an aspect, the shale inhibitor can include a salt (e.g., potassium chloride (KCl), sodium chloride (NaCl)), a polymer (e.g., a high molecular weight polymer (e.g., a polyacrylamide)), a charged polymer, or a combination thereof. For example, the shale inhibitor can include an amine functional group, (e.g., a primary amine functional group, a secondary amine functional group, a tertiary amine functional group, or combinations thereof) and/or a protonated amine functional group (e.g., a protonated primary amine functional group, a protonated secondary amine functional group, a protonated tertiary amine functional group, or combinations thereof). Without wishing to be limited by theory, amine functional groups and/or protonated amine functional groups in the amine-based shale inhibitor can form hydrogen bonds with the clay (i.e., with the water and/or hydroxyl groups present in the clay), thereby inhibiting water adsorption by the clay material, for example by blocking sites available for hydrogen bonding and rendering such sites unavailable for hydrogen bonding with water molecules. Further, without wishing to be limited by theory, the shale inhibitor may minimize shale or clay hydration and thus prevent or reduce the adsorption of water by downhole water-reactive formations to prevent or reduce a loss of wellbore and/or subterranean formation stability. In embodiments, the shale inhibitor is not an amine-based shale inhibitor.

In an aspect, a shale inhibitor may be included within the WSF in a suitable or effective amount (e.g., an amount effective to provide desired shale inhibitory properties to the WSF). The resultant amount of shale inhibitor that is necessary to impart desired shale inhibitory properties to a WSF may be dependent upon a variety of factors such as the composition of the WSF; the presence or absence of various additives in the WSF; the intended formation location where the WSF is expected to be used to inhibit water uptake; the composition of the formation; the pressure of the formation; the temperature of the formation; the diameter of the hole; and the like; or combinations thereof.

In an aspect, a shale inhibitor may be present within the WSF in an amount (e.g., target amount) of from about 0.01 wt. % to about 5 wt. %, alternatively from about 0.02 wt. % to about 4 wt. %, or alternatively from about 0.03 wt. % to about 3 wt. %, based on the total weight of the WSF. For purposes of the disclosure herein, the target amount of shale inhibitor in the WSF refers to the desired amount of shale inhibitor in the WSF; e.g., the amount of shale inhibitor effective to provide desired shale inhibitory properties to the WSF.

The WSF may further include additional additives as deemed appropriate for improving the properties of the fluid. Such additives may vary depending on the intended use of the fluid in the wellbore. Examples of such additives include, but are not limited to suspending agents, density reducing additives, settling prevention agents, expansion additives, clays, salts, accelerants, set retarders, lignosulfonates, defoamers, surfactants, dispersing agents, fluid loss control agents, weighting materials, dispersants, fillers, zeolites, barite, calcium sulfate, silica flour, sand, slag, vitrified shale, fly ash, pozzolanic ash, lime, formation conditioning agents, fluid absorbing materials, resins, aqueous superabsorbers, viscosifying agents, gelling agents, crosslinkers, mechanical property modifying additives, elastomers, styrene-butadiene copolymers, conventional reinforcing materials, carbon fibers, glass fibers, metal fibers, minerals fibers, and the like, or combinations thereof. These additives may be introduced singularly or in combination using any suitable methodology and in amounts effective to produce the desired improvements in the properties of the WSF. As will be appreciated by one of skill in the art with the help of this disclosure, any of the components and/or additives used in the WSF should be compatible with the shale inhibitor used in the WSF composition.

In an aspect, the WSF as disclosed herein may be prepared by using any suitable method or process. The components of the WSF (e.g., shale inhibitor, base fluid, additives, etc.) may be combined and mixed in by using any mixing device compatible with the composition, e.g., a mixer, a batch mixer, a batch mixer with impellers and/or paddles, a blender, a batch blender, single ribbon type blenders, double ribbon type blenders, horizontal blenders, vertical blenders, inclined blenders, single or double ribbon type blenders which could further be horizontal, vertical or inclined, mixing eductors, dry powder eductors, dry powder eductor with centrifugal pump followed by circulation loop, cyclone-type dry to liquid mixer, inline static mixers, and the like, or any suitable combination thereof.

In an aspect, the components of the WSF are combined at the well site; alternatively, the components of the WSF are combined off-site and are transported to and used at the well site. The resulting WSF may be pumped downhole where it may function as intended (e.g., prevent and/or reduce water uptake by water-reactive formations).

As will be appreciated by one of skill in the art, and with the help of this disclosure, a WSF including a shale inhibitor and/or salt as disclosed herein may be used for preventing and/or reducing water uptake by water-reactive formations in any suitable stage of a wellbore's life, such as for example, during a drilling operation, completion operation, etc.

In an aspect, a method of servicing a wellbore in a subterranean formation can include detecting a shale inhibitor and/or salt in a WSF (e.g., testing the WSF for the presence and/or amount of shale inhibitor and/or salt in the WSF).

In some aspects, the shale inhibitor and/or salt may be detected in a WSF prior to using the WSF in a wellbore servicing operation (e.g., a first amount or concentration that is determined prior to placing the WSF in the wellbore and/or subterranean formation, prior to circulating the WSF in the wellbore and/or subterranean formation); as will be discussed in more detail later herein. In such aspects, the shale inhibitor and/or salt may be detected in a WSF at any suitable time between preparing the WSF and placing the WSF in the wellbore and/or subterranean formation. In such aspects, the WSF can be placed in the wellbore and/or subterranean formation subsequent to determining the amount of shale inhibitor and/or salt in the WSF (e.g., post-testing of the WSF for the presence and/or amount of shale inhibitor and/or salt in the WSF). In aspects, prior to using the WSF in a wellbore servicing operation, the WSF does not include a shale inhibitor and/or a salt.

As will be appreciated by one of skill in the art, and with the help of this disclosure, determining the concentration (e.g., a first concentration) of the shale inhibitor and/or salt in the WSF subsequent to adding a known amount (e.g., target amount) of shale inhibitor and/or salt to the WSF (and prior to use thereof via placement in a wellbore) may provide validation of the detection method and/or may allow for calibrating the detection method by reconciling the known amount (e.g., target amount) of shale inhibitor and/or salt added to the WSF with the detected amount. In aspects where the known amount (e.g., target amount) of shale inhibitor and/or salt added to the WSF and the detected amount are the same, no action is needed (e.g., no reconciliation is necessary). In aspects where the known amount (e.g., target amount) of shale inhibitor and/or salt added to the WSF and the detected amount are different, a correction factor can be employed to reconcile (e.g., correlate) the known amount (e.g., target amount) of shale inhibitor and/or salt added to the WSF with the detected amount. As will be appreciated by one of skill in the art, and with the help of this disclosure, the method of detecting the amount of shale inhibitor and/or salt in the WSF might either overestimate or underestimate the actual amount (e.g., known amount, target amount) of shale inhibitor and/or salt added to the WSF. For example, a correction factor could be calculated by dividing the detected (e.g., measured, calculated) amount of shale inhibitor and/or salt in the WSF by the actual amount (e.g., known amount, target amount) of shale inhibitor and/or salt added to the WSF; or by dividing the actual amount (e.g., known amount, target amount) of shale inhibitor and/or salt added to the WSF by the detected (e.g., measured, calculated) amount of shale inhibitor and/or salt in the WSF. The correction factor (e.g., correlation factor) can be used to correlate the known amount (e.g., target amount) of shale inhibitor and/or salt added to the WSF with the detected amount. The correction factor (e.g., correlation factor) can be further used throughout testing of the WSF (e.g., subsequent to placing the WSF in a wellbore and/or subterranean formation) to provide for a more accurate determination of the amount of shale inhibitor and/or salt in the WSF.

In other aspects, the shale inhibitor and/or salt may be detected in a WSF subsequent to using the WSF in a wellbore servicing operation (e.g., a second amount or concentration that is determined subsequent to placing the WSF in the wellbore and/or subterranean formation, subsequent to circulating the WSF in the wellbore and/or subterranean formation); as will be discussed in more detail later herein. In such aspects, the WSF may be placed in the wellbore and/or subterranean formation pre-testing of the WSF for the presence and/or amount of shale inhibitor and/or salt in the WSF. In aspects, only the first or the second amount or concentration of the shale inhibitor and/or the salt is determined. For example, in aspects determination of a concentration of a salt is performed subsequent to using the WSF in a wellbore servicing operation.

In an aspect, the WSF may be utilized in a drilling and completion operation.

In an aspect, the WSF is a drilling fluid. A drilling fluid, also known as a drilling mud or simply "mud," is a fluid that is circulated through a wellbore to yield a circulated drilling fluid, while the wellbore is being drilled to facilitate the drilling operation. Generally, a circulated drilling fluid can carry cuttings up from downhole and around a drill bit, transport them up an annulus, and allow their separation, followed by recycling the drilling fluid to the drilling operation. Further, a drilling fluid can cool and lubricate the drill bit, as well as reduce friction between a drill string and the sides of the wellbore hole. Furthermore, the drilling fluid aids in support of a drill pipe and drill bit, and provides a hydrostatic pressure necessary to maintain the integrity of the wellbore walls and prevent well blowouts. The shale inhibitor and/or salt in the drilling fluid may contact the subterranean formation. When the subterranean formation includes clay and/or shale, at least a portion of the shale inhibitor and/or salt may interact with the subterranean formation to prevent and/or reduce water uptake by such water-reactive formation (for example, and without wishing to be limited by theory, by forming a physical bond such as a hydrogen bond with the clay), wherein at least a portion of the shale inhibitor and/or salt may be retained by the subterranean formation, thereby depleting (e.g., reducing the amount of) the shale inhibitor and/or salt in the drilling fluid. Salt may be incorporated into the drilling fluid from the formation during the drilling operation. Depending on the amount of shale inhibitor and/or salt detected in the circulated drilling fluid, the amount of shale inhibitor and/or salt in the drilling fluid may be adjusted (e.g., increased or decreased) as necessary, as will be discussed in more detail later herein.

In an aspect, the WSF (e.g., including the shale inhibitor and/or salt) is a completion fluid. In an aspect, when desired (for example, upon the cessation of drilling operations and/or upon reaching a desired depth), the wellbore or a portion thereof may be prepared for completion. In an aspect, the method of using a WSF (e.g., including shale inhibitor and/or salt, such as a completion fluid including an shale inhibitor and/or salt) may include completing the wellbore. Typically, completion fluids are free of solids. Generally, a completion fluid is placed in the well to facilitate final operations prior to initiation of production, such as setting screens, production liners, packers, downhole valves, etc. The wellbore, or a portion thereof, may be completed by providing a casing string within the wellbore and cementing or otherwise securing the casing string within the wellbore. In such an aspect, the casing string may be positioned (e.g., lowered into) the wellbore to a desired depth prior to, concurrent with, or following provision of the completion fluid. The completion fluid may be displaced from the wellbore by pumping a flushing fluid, a spacer fluid, and/or a suitable cementitious slurry downward through an interior flowbore of the casing string and into an annular space formed by the casing string and the wellbore walls. When the cementitious slurry has been positioned, the cementitious slurry may be allowed to set. The shale inhibitor and/or salt in the completion fluid may contact the subterranean formation whereby an amount of the shale inhibitor and/or salt in the completion may increase or decrease. For example, when the subterranean formation includes clay and/or shale, at least a portion of the shale inhibitor and/or salt may interact with the subterranean formation to prevent and/or reduce water uptake by such water-reactive formation (for example, and without wishing to be limited by theory, by forming a physical bond such as a hydrogen bond with the clay), wherein at least a portion of the shale inhibitor and/or salt may be retained by the subterranean formation, thereby depleting (e.g., reducing the amount of) the shale inhibitor and/or salt in the completion fluid. Depending on the amount of shale inhibitor and/or salt detected in the displaced completion fluid, the amount of shale inhibitor and/or salt introduced to the subterranean formation (for example via a flushing fluid, a spacer fluid, and/or a suitable cementitious slurry used to displace the completion fluid) may be adjusted as necessary, as will be discussed in more detail later herein.

In an aspect, a method of detecting a shale inhibitor and/or salt in a WSF can include contacting an aliquot of the WSF with a detector compound to form a detection solution. For purposes of the disclosure herein, an aliquot of a liquid (e.g., WSF) refers to an amount of the liquid that is sufficient for allowing the detection of a shale inhibitor and/or salt. For example, an aliquot of the WSF can be equal to or greater than about 0.001 milliliters (mL), alternatively equal to or greater than about 0.01 mL, alternatively equal to or greater than about 0.1 mL, alternatively equal to or greater than about 1 mL, alternatively equal to or greater than about 5 mL, alternatively equal to or greater than about 10 mL, or alternatively equal to or greater than about 25 mL.

In aspects where the WSF is substantially solids-free, an aliquot of the WSF can be contacted with the detector compound without any further processing. For purposes of the disclosure herein, a liquid is considered substantially solids-free when the amount of solids in the WSF does not interfere with the detection of the shale inhibitor and/or salt. As will be appreciated by one of skill in the art, and with the help of this disclosure, whether solids present in the WSF interfere with the detection of the shale inhibitor and/or salt is dependent upon a variety of factors, such as the amount of solids, the size and/or size distribution of solids, the light absorbing properties of the solids, the light diffraction properties of the solids, etc. For example, a substantially solids-free WSF may include solids in an amount of less than about 1 wt. %, alternatively less than about 0.1 wt. %, alternatively less than about 0.01 wt. %, alternatively less than about 0.001 wt. %, or alternatively less than about 0.0001 wt. %, based on the total weight of the WSF.

In aspects where the WSF includes solids (e.g., the WSF includes solids that may interfere with the detection of the shale inhibitor and/or salt), at least a portion of the WSF may be subjected to a solids removal procedure to yield a substantially solids-free WSF. The solids in the WSF can be debris, mud, WSF additives, drill cuttings, and the like, or combinations thereof. In an aspect, the solids removal procedure can be selected from the group that includes at least filtration, sedimentation, decantation, centrifugation, screening, chemical dissolution, and combinations thereof. For example, at least a portion of the WSF including an undesirable amount of solids (e.g., solids that may interfere with the detection of the shale inhibitor and/or salt) may be filtered (e.g., via any suitable filter, such as a syringe filter) to yield a filtrate (passing through a filter) and solids (retained onto a filter), wherein the filtrate is the substantially solids-free WSF and may be further subjected to shale inhibitor and/or salt detection as disclosed herein. As another example, at least a portion of the WSF including an undesirable amount of solids (e.g., solids that may interfere with the detection of the shale inhibitor and/or salt) may be contacted with a chemical compound that may convert the solids into soluble compounds (e.g., acid soluble particles could be dissolved with an acid), thereby yielding the substantially solids-free WSF which may be further subjected to shale inhibitor and/or salt detection as disclosed herein. An aliquot of the substantially solids-free WSF (e.g., an aliquot of the filtrate) can be contacted with a detector compound to form the detection solution.

In some aspects, the WSF may be subjected to more than one solids removal procedure to yield a substantially solids-free WSF. For example, a circulated drilling fluid may be subjected to centrifugation or screening for the removal of cuttings, wherein the resulting WSF is not solids-free and may be recycled to circulating in the wellbore and/or subterranean formation; and wherein an aliquot of the resulting WSF may be subjected to an additional solids removal procedure, such as filtration, to yield an aliquot of the WSF that is substantially solids-free and may be further subjected to shale inhibitor and/or salt detection as disclosed herein.

As will be appreciated by one of skill in the art, and with the help of this disclosure, the amount of WSF subjected to a solids removal procedure to yield a substantially solids-free WSF can be greater than the aliquot of the substantially solids-free WSF contacted with a detector compound to form the detection solution, for example to allow for more than one aliquot to be subjected to the detection method. Alternatively, the amount of WSF subjected to a solids removal procedure to yield a substantially solids-free WSF can be about the same as the aliquot of the substantially solids-free WSF contacted with a detector compound to form the detection solution.

In an aspect, the detector compound can include any suitable compound that can undergo a chemical reaction with the shale inhibitor and/or the salt and produce a colored reaction product that has the ability to impart a color and/or color intensity to the detection solution that is different from the color and/or color intensity, respectively, of the aliquot of the WSF subjected to detection as disclosed herein. As will be appreciated by one of skill in the art, and with the help of this disclosure, if the detector compound is colored, the color and/or color intensity of the detection solution is different from the color and/or color intensity, respectively, of the detector compound. In an aspect, the detector compound is chromophore, for example a chromophore of the type suitable for use with a detector such as Water Lens test kit as described herein.

Nonlimiting examples of detector compounds suitable for use in the present disclosure include methylene blue, ninhydrin, indane-1,2,3-trione, hydrantin, quinhydrone, Dragendorff reagent, chloranil, N-halosuccinimide, N-bromosuccinimide, N-iodosuccinimide, a hydrazo compound, a diazonium salt, fluorescein, fluorescein halide, fluorescein chloride, and the like, or combinations thereof.

The detector compounds as disclosed herein, when combined with the shale inhibitor and/or the salt, can undergo a chemical reaction with the shale inhibitor and/or the salt, respectively, and produce a colored reaction product.

In an aspect, the detector compound can be contacted in any suitable amount with an aliquot of the WSF to yield the detection solution. For example, the detector compound can be contacted with an aliquot of the WSF in an amount of from about 0.01 mmol/liter to about 200 mmol/liter, alternatively from about 0.1 mmol/liter to about 150 mmol/liter, alternatively from about 1 mmol/liter to about 100 mmol/liter, or alternatively from about 1 mmol/liter to about 50 mmol/liter detector compound, based on the total volume of the detection solution.

Without wishing to be limited by theory, and as will be appreciated by one of skill in the art, and with the help of this disclosure, color and/or color intensity can be detected by optical detection. For purposes of the disclosure herein, the term "optical detection" refers to detection performed visually by a human subject (e.g., an observation by an operator) and/or detection performed by a machine, for example detection with a spectrometer (e.g., ultraviolet-visible (UV-VIS) spectrometer and/or colorimeter) by using an analytical technique, such as UV-VIS spectroscopy and/or colorimetry, respectively.

In aspects, the color and/or color intensity can be detected by an analyzer, such as a Water Lens test kit available from Water Lens, LLC in Houston, Tex. Such a Water Lens test kit utilizes several independent detection motifs in a 96-well plate format. Each 8-well strip (12 strips to a plate) is filled with a different assay, each of which contains a detector compound such as a colorimetric dye (and optionally other constituents) sensitive to the presence of the component(s)/analyte(s) (e.g., the shale inhibitor(s) and/or the salt(s)) being measured. The assays can then be freeze-dried, which can provide for a long shelf life, even in harsh environments, and rapid rehydration upon introduction of the sample of wellbore servicing fluid. The tests can be carefully formulated to be compatible with specific analytes.

The analyzer (e.g., Water Lens test kit) can include a colorimeter that operates on the principle of colorimetric absorption by photosensitive dyes (e.g., one or more detector compounds such as dyes including chromophores). When the dyes bind to respective analytes, the photometric spectra of the dyes change. These changes can be read by monitoring the absorbance of light at specific wavelengths as light passes through the sample(s). The absorbance characteristics can be read by a colorimeter, and the data generated can be used to calculate the concentration of the particular analyte in each sample of the wellbore servicing fluid, for example via software.

Generally, color is associated specifically with electromagnetic radiation (e.g., visible light) of a certain range of wavelengths visible to the human eye, for example electromagnetic radiation with a wavelength between about 380 nanometers (nm) and about 760 nm (visible spectrum). When all wavelengths of visible light are present, the light appears "white" to a human. Colored materials (e.g., compounds, solids, liquids, solutions, gases) are colored because of the absorption of visible light (e.g., visible electromagnetic radiation). The color is a result of the material absorbing a certain color of light, leading to the visual perception of the compound being the complementary color. If any wavelength is removed (absorbed) from the visible light, a human perceives the remaining combination of wavelengths of light as the "complementary" color. For example, when light passes through a liquid (e.g., colored solution), a characteristic portion of wavelengths can be absorbed. If wavelengths of light from a certain region of the spectrum are absorbed by a material, then the materials will appear to be the complementary color to a human operator. For example, if violet light with wavelength of 400 nm is absorbed by a liquid, the liquid will visually appear yellow. As another example, if blue light with wavelength of 450 nm is absorbed by a liquid, the liquid will visually appear orange. As yet another example, if green light with wavelength of 530 nm is absorbed by a liquid, the liquid will visually appear purple.

In an aspect, the detection solution can be characterized by at least one absorption peak wavelength in the range of from about 380 nm to about 760 nm, alternatively from about 390 nm to about 750 nm, alternatively from about 400 nm to about 740 nm, alternatively from about 380 nm to about 460 nm, or alternatively from about 460 nm to about 760 nm. In such aspect, the detection solution is characterized by a visible color (e.g., a color that can be visually perceived by a human upon visual observation of the detection solution), thereby the detection of the shale inhibitor and/or the salt can be performed via optical detection (e.g., visual detection and/or spectroscopic detection). For purposes of the disclosure herein, the terms "absorption peak wavelength," "maximum absorption wavelength," and "wavelength of maximum absorbance" ($\lambda_{max}$) can be used interchangeably, and refer to the wavelength where a specific compound or mixture of compounds displays the highest absorbance (i.e., the highest absorption intensity) at a given concentration. As will be appreciated by one of skill in the art, and with the help of this disclosure, a specific compound or mixture of compounds can be characterized by a local maximum absorbance and/or an absolute maximum absorbance, wherein the local maximum absorbance refers to the maximum absorbance intensity in a given wavelength range (e.g., the maximum absorbance intensity in a wavelength range of from about 500 nm to about 600 nm), and wherein the absolute maximum absorbance refers to the maximum absorbance intensity across the entire investigated wavelength range (e.g., the maximum absorbance intensity across the entire wavelength range of from about 380 nm to about 760 nm). Further, and as will be appreciated by one of skill in the art, and with the help of this disclosure, when a specific compound or mixture of compounds displays a single absorption peak across the entire investigated wavelength range, the local maximum absorbance and the absolute maximum absorbance are the same; and when a specific compound or mixture of compounds displays two or more absorption peaks across the entire investigated wavelength range, the peak with the highest absorption intensity across the entire investigated wavelength range displays the absolute maximum absorbance, while the peaks other than the peak with the highest absorption intensity display local maximum absorbances. Furthermore, and as will be appreciated by one of skill in the art, and with the help of this disclosure, an absorption peak wavelength may correspond to a local maximum absorbance and/or an absolute maximum absorbance. Absorption peak wavelengths are characteristic to each colored compound.

Generally, and without wishing to be limited by theory, colorimetry is an analytical technique (e.g., spectroscopic technique) that can be used to determine the amount (e.g., concentration) of colored compounds in solutions by the application of the Beer-Lambert law, which states that the concentration of a solute is proportional to the absorbance (i.e., absorption intensity). Typically, colorimetry uses the entire visible spectrum (i.e., white light or visible light) or light with a specific wavelength, thereby allowing for the complementary color of the absorbed radiation to be observed as transmitted light. Colorimetry can use a particular wavelength when the compound to be detected is known, and consequently the wavelength at which such compound absorbs is known. Colorimetry does not scan the entire visible light spectrum (as opposed to UV-VIS spectroscopy). Further, colorimetry does not employ a reference sample concurrently with a colored sample for detection. Colorimetry is performed with a colorimeter. A colorimeter may analyze a sample in a laboratory setting. Alternatively, a portable colorimeter may be employed for sample analysis in the field (i.e., on location; in real-time).

In an aspect, a method of detecting a shale inhibitor and/or a salt in a WSF can include detecting an absorption intensity for the detection solution at a wavelength within about ±20%, alternatively within about ±10%, alternatively within about ±5%, alternatively within about ±1% of the at least one absorption peak wavelength ($\lambda_{max}$), or alternatively at about the at least one absorption peak wavelength ($\lambda_{max}$). Generally, and without wishing to be limited by theory, across the light spectrum wavelengths, colored compounds absorb radiation via peaks (as opposed to lines), owing to complex electronic transitions within the molecules of the colored compounds. Further, and without wishing to be limited by theory, the absorption intensity can be measured at any wavelength under the absorption peak; however, measuring the absorption intensity at the at least one absorption peak wavelength ($\lambda_{max}$) will yield the greatest detection sensitivity (owing to the steepest slope of a calibration curve relating absorption intensity to concentration). Furthermore, and without wishing to be limited by theory, the absorption intensity is proportional to the amount (e.g., concentration) of colored compound (e.g., colored reaction product formed by the chemical reaction between the shale inhibitor and/or salt and the detector compound), in accordance with the Beer-Lambert law. As will be appreciated by one of skill in the art, and with the help of this disclosure, the further the wavelength at which the absorption intensity is measured is from the at least one absorption peak wavelength ($\lambda_{max}$), the greater the error in determining the amount (e.g., concentration) of colored compound (e.g., colored reaction product formed by the chemical reaction between the shale inhibitor and/or salt and the detector compound).

In an aspect, detecting an absorption intensity for the detection solution at a wavelength within about ±20% of the at least one absorption peak wavelength ($\lambda_{max}$) can include visually detecting the color intensity of the detection solution. For example, a human (e.g., an operator) can visually detect the color intensity of the solution, such as deep purple versus light purple, mildly deep red versus extremely deep red.

In an aspect, detecting an absorption intensity for the detection solution at a wavelength within about ±20% of the at least one absorption peak wavelength ($\lambda_{max}$) can include spectroscopically detecting an absorption intensity of the detection solution, for example via colorimetry and/or UV-VIS spectroscopy, as disclosed herein.

In an aspect, a method of detecting a shale inhibitor and/or salt in a WSF can further include heating the detection solution, e.g., heating the detection solution prior to detecting an absorption intensity for the detection solution at a wavelength within about ±20% of the at least one absorption peak wavelength. The detection solution can be heated by using any suitable methodology (e.g., a heater, a heat exchanger, a fired heater, a burner, a heating mantle, a heating element, etc.).

In an aspect, the detection mixture can be heated to a temperature of from about 30° C. to about a boiling point of the detection solution, alternatively from about 30° C. to about 100° C., alternatively from about 35° C. to about 95° C., alternatively from about 40° C. to about 90° C., or alternatively from about 50° C. to about 75° C. Without wishing to be limited by theory, heating the detection solution can speed up (e.g., increase the rate of) the reaction between the detector compound and the shale inhibitor and/or the salt. As will be appreciated by one of skill in the art, and with the help of this disclosure, and without wishing to be limited by theory, colored compounds absorbance generally varies with temperature, and consequently the heated detection solution can be cooled to ambient temperature (e.g., room temperature, a temperature of from about 15° C. to about 30° C.) prior to detecting an absorption intensity for the detection solution at a wavelength within about ±20% of the at least one absorption peak wavelength. For example, the detection solution may be allowed to reach ambient temperature by losing heat to the surrounding environment. As another example, the detection solution can be cooled by using any suitable methodology (e.g., a cooler, a heat exchanger, a cooling bath, an ice bath, a cooling element, etc.).

In an aspect, a method of detecting a shale inhibitor and/or salt in a WSF can include comparing the absorption intensity of the detection solution at the wavelength within about ±20% of the at least one absorption peak wavelength ($\lambda_{max}$) with a target absorption intensity of the shale inhibitor and/or the salt, respectively, to determine the amount of shale inhibitor and/or salt in the WSF.

In an aspect, comparing the absorption intensity of the detection solution at the wavelength within about ±20% of the at least one absorption peak wavelength ($\lambda_{max}$) with a target absorption intensity of the shale inhibitor and/or salt includes optically comparing the color and/or color intensity of the detection solution with a target color and/or color intensity, respectively. For purposes of the disclosure herein, the terms "optically comparing" and "optical comparison" refers to a comparison performed visually by a human subject (e.g., an operator) and/or a comparison performed by a machine, such as a computing device (e.g., computer, laptop, calculator, etc.) used in conjunction with (e.g., connected to, networked with, etc.) a spectrometer (e.g., UV-VIS spectrometer and/or colorimeter).

In an aspect, determining the amount of shale inhibitor and/or salt in the WSF further includes visually comparing a visually observed color and/or color intensity of the detection solution with a reference color chart that correlates color and/or color intensity, respectively, with the amount of the shale inhibitor and/or salt. In an aspect, a reference color chart can be constructed for each detector compound, given that each detector compound might provide for a detection solution having a different color or a different color hue. For example, it is easier to visually compare a red color to a reference color chart that employs the same red color than it is to compare a red color to a reference color chart that employs a red color having an orange hue. A reference color chart can be constructed for a specific detector compound by preparing detection solutions having known concentrations of the shale inhibitor and/or salt, and recording the color corresponding to each concentration, for example by taking a picture of the detection solution, and noting the concentration of the shale inhibitor and/or salt that corresponds to the color and color intensity in the picture. The reference color chart can generally include two or more pictures relating the color and color intensity of the detection solution to corresponding known concentrations of the shale inhibitor and/or salt. As will be appreciated by one of skill in the art, and with the help of this disclosure, and without wishing to be limited by theory, the higher the concentration of the shale inhibitor and/or salt, the more intense (e.g., deeper) the color of the detection solution; and the lower the concentration of the shale inhibitor and/or salt, the less intense (e.g., paler) the color of the detection solution.

As will be appreciated by one of skill in the art, and with the help of this disclosure, when the color of the detection solution changes based on the type of shale inhibitor and/or salt as well as the detector compound (e.g., some detector compounds may yield one color for shale inhibitors including primary amines, and a different color for shale inhibitors including secondary and/or tertiary amines), it may be necessary to create a reference color chart for a specific detector compound used in conjunction (e.g., paired) with a specific shale inhibitor and/or salt. Further, and as will be appreciated by one of skill in the art, and with the help of this disclosure, while as little as two concentrations (e.g., a low concentration and a high concentration) can be used for creating a reference color chart, using more than two, alternatively more than three, alternatively more than four, alternatively more than five, alternatively from three to about twenty, alternatively from about five to about fifteen, or alternatively from about five to about ten concentrations for creating a reference color chart can significantly improve the accuracy of determining the amount of shale inhibitor and/or salt in the WSF.

In some aspects, visually comparing the color and/or color intensity of the detection solution with the reference color chart can include matching the color and/or color intensity of the detection solution with the closest color and/or color intensity, respectively, on the reference color chart, wherein the closest color and/or color intensity determines the amount of the shale inhibitor and/or salt in the WSF. In other aspects, visually comparing the color and/or color intensity of the detection solution with the reference color chart can include matching the color and/or color intensity of the detection solution with the closest two colors and/or color intensities, respectively, on the reference color chart, followed by estimating the amount of the shale inhibitor and/or salt in the WSF between the amounts corresponding to the closest two colors and/or color intensities, respectively.

In some aspects, the reference color chart can include images or pictures of detection solutions correlated with known concentrations of the shale inhibitor and/or salt printed on an appropriate substrate, such as paper (e.g., paper reference color chart), cardboard (e.g., cardboard reference color chart), metal (e.g., metal reference color chart), plastic (e.g., plastic reference color chart), and the like, or combinations thereof. In other aspects, the reference color chart including images or pictures of detection solutions correlated with known concentrations of the shale inhibitor and/or salt can be displayed on an electronic screen, such as a computer monitor, a laptop monitor, a phone screen, and the like, or combinations thereof.

In an aspect, comparing the absorption intensity of the detection solution at the wavelength within about ±20% of the at least one absorption peak wavelength ($\lambda_{max}$) with a target absorption intensity of the shale inhibitor and/or salt includes using a calibration curve that correlates absorption intensity at the wavelength within about ±20% of the at least one absorption peak wavelength ($\lambda_{max}$) with the amount of the shale inhibitor and/or salt (e.g., known amount of the shale inhibitor and/or salt).

In an aspect, a calibration curve can be constructed for each detector compound, given that each detector compound might provide for a detection solution having a different absorption peak wavelength ($\lambda_{max}$) (e.g., different color or a different color hue). A calibration curve can be constructed for a specific detector compound by preparing detection solutions having known concentrations of the shale inhibitor and/or salt; subjecting the detection solutions to spectroscopy (e.g., UV-VIS spectroscopy and/or colorimetry); and plotting the known concentrations of the shale inhibitor and/or salt as a function of the corresponding measured absorption intensity. As will be appreciated by one of skill in the art, and with the help of this disclosure, while the calibration curve can be constructed (e.g., drawn) with as little as two absorption intensity measurements corresponding to two different known concentrations of the shale inhibitor and/or salt, at least three absorption intensity measurements corresponding to three different known concentrations of the shale inhibitor and/or salt can be used for constructing the calibration curve, preferably as many absorption intensity measurements as it is deemed to be statistically significant for any particular case (e.g., any particular detector compound, any particular pair of detector compound and shale inhibitor and/or salt).

Further, without wishing to be limited by theory, and as will be appreciated by one of skill in the art, and with the help of this disclosure, a calibration curve is generally accompanied by a mathematical equation describing the calibration curve, and the mathematical equation can be used as well for translating the absorption intensity into the amount of shale inhibitor and/or salt in the WSF, for example by entering into the equation the measured absorption intensity and calculating the corresponding amount of shale inhibitor and/or salt in the WSF.

Furthermore, as will be appreciated by one of skill in the art, and with the help of this disclosure, sometimes spectrometers (e.g., colorimeter, portable colorimeter, UV-VIS spectrometer, portable UV-VIS spectrometer) can display a systematic error or bias, and as such it may be desired to construct the calibration curve with the same spectrometer that is used for measuring the absorption intensity.

In an aspect, a method of detecting a shale inhibitor and/or salt in a WSF can include comparing the amount of shale inhibitor and/or salt in the WSF with a target amount of the shale inhibitor and/or salt.

In some aspects, the amount of shale inhibitor and/or salt in the WSF can be about the same as the target amount of the shale inhibitor and/or salt. In such aspects, the WSF can be placed in the wellbore and/or subterranean formation where it may function as intended (e.g., prevent and/or reduce water uptake by water-reactive formations).

In other aspects, the amount of shale inhibitor and/or salt in the WSF can be different (e.g., less, lower, more, greater) than the target amount of the shale inhibitor and/or salt. In such aspects, the determined amount of shale inhibitor and/or salt in the WSF can indicate a variance between the actual amount of the shale inhibitor and/or salt in the WSF and the desired or target amount of the shale inhibitor and/or salt. For example, such variance can range from greater than about 0% (e.g., wherein very little shale inhibitor and/or salt has been depleted from or incorporated into the WSF, for example shale inhibitor and/or salt being lost to the formation or salt being incorporated from the formation) to about 100% (e.g., wherein substantially all of the shale inhibitor and/or salt has been depleted from the WSF, for example by being lost to the formation).

In an aspect, the amount of shale inhibitor and/or salt in the WSF can be lower than the target amount of the shale inhibitor and/or the salt, respectively. For example, the amount of shale inhibitor and/or salt in the WSF can be equal to or greater than about 1%, alternatively equal to or greater than about 5%, alternatively equal to or greater than about 10%, alternatively equal to or greater than about 15%, alternatively equal to or greater than about 20%, alternatively equal to or greater than about 25%, alternatively equal to or greater than about 30%, alternatively equal to or greater than about 35%, alternatively equal to or greater than about 40%, alternatively equal to or greater than about 45%, alternatively equal to or greater than about 50%, alternatively equal to or greater than about 55%, alternatively equal to or greater than about 60%, alternatively equal to or greater than about 65%, alternatively equal to or greater than about 70%, alternatively equal to or greater than about 75%, alternatively equal to or greater than about 80%, alternatively equal to or greater than about 85%, alternatively equal to or greater than about 90%, alternatively equal to or greater than about 95%, alternatively equal to or greater than about 99%, or alternatively about 100% lower than the target amount of the shale inhibitor and/or salt. In some aspects, the amount of shale inhibitor and/or salt in the WSF can be greater than the target amount of the shale inhibitor and/or the salt, respectively. For example, during a drilling operation, the WSF may encounter different formation layers that require different levels of inhibition (e.g., require different concentrations of shale inhibitor and/or salt), and as such the WSF may have an amount of shale inhibitor and/or salt that is greater than the amount required in a specific portion of the subterranean formation. As will be appreciated by one of skill in the art, and with the help of this disclosure, the amount of shale inhibitor and/or salt in the WSF may be increased over time, for example as a result of encountering more reactive formations.

In some aspects, the amount of shale inhibitor and/or salt in the WSF can be less than the target amount of the shale inhibitor and/or salt by a threshold amount. For purposes of the disclosure herein, the threshold amount of shale inhibitor and/or salt is defined as the difference between the amount (e.g., actual amount, measured amount) of shale inhibitor and/or salt in the WSF and the target amount of the shale inhibitor and/or the salt, respectively. Further, for purposes of the disclosure herein, the threshold amount of shale inhibitor and/or salt refers to the amount of shale inhibitor and/or salt that is "missing" from the WSF (e.g., the amount of shale inhibitor and/or salt that has been depleted from the WSF, for example by being lost to the formation) and which requires supplementation of shale inhibitor and/or salt into the WSF, in order to provide for a WSF having the target amount of the shale inhibitor and/or the salt, respectively.

In aspects where the amount of shale inhibitor and/or salt in the WSF is less than the target amount of the shale inhibitor and/or the salt, respectively, by an amount that is equal to or greater than a threshold amount, the WSF may require further processing prior to being used in a wellbore servicing operation (e.g., supplemental shale inhibitor and/or salt may be added to the WSF, in order to provide for a WSF having the target amount of the shale inhibitor and/or the salt, respectively).

As will be appreciated by one of skill in the art, and with the help of this disclosure, the threshold amount of shale inhibitor and/or salt that dictates whether a WSF requires or does not require addition of supplemental shale inhibitor, salt, and/or base fluid, may depend on a variety of factors, such as the type of wellbore servicing operation, the composition of the WSF, the type and/or configuration of the wellbore, the type of subterranean formation, the subterranean formation conditions (e.g., temperature, pressure, etc.), and the like, or combinations thereof.

The threshold amount of shale inhibitor and/or salt can be expressed as a percentage (%) of the target amount of the shale inhibitor and/or the salt, respectively. For example, the threshold amount of shale inhibitor and/or salt can be equal to or greater than about 1%, alternatively equal to or greater than about 5%, alternatively equal to or greater than about 10%, alternatively equal to or greater than about 15%, alternatively equal to or greater than about 20%, alternatively equal to or greater than about 25%, alternatively equal to or greater than about 30%, alternatively equal to or greater than about 35%, alternatively equal to or greater than about 40%, alternatively equal to or greater than about 45%, alternatively equal to or greater than about 50%, alternatively equal to or greater than about 55%, alternatively equal to or greater than about 60%, alternatively equal to or greater than about 65%, alternatively equal to or greater than about 70%, alternatively equal to or greater than about 75%, alternatively equal to or greater than about 80%, alternatively equal to or greater than about 85%, alternatively equal to or greater than about 90%, alternatively equal to or greater than about 95%, alternatively equal to or greater than about 99%, or alternatively about 100% of the target amount of the shale inhibitor and/or the salt, respectively.

In aspects where the amount of shale inhibitor and/or salt in the WSF is less than the target amount of the shale inhibitor and/or the salt, respectively, by an amount that is lower than the threshold amount, the WSF may be used in a wellbore servicing operation without further processing (e.g., without adding supplemental shale inhibitor and/or salt to the WSF). For example, at least a portion of the WSF may be placed in the wellbore and/or subterranean formation where it may function as intended (e.g., prevent and/or reduce water uptake by water-reactive formations).

In some aspects, the amount of shale inhibitor and/or salt in the WSF can be greater than the target amount of the shale inhibitor and/or the salt, respectively. In aspects where the amount of shale inhibitor and/or salt in the WSF is greater than the target amount of the shale inhibitor and/or the salt, respectively, the WSF may be used in a wellbore servicing operation without further processing (e.g., without adjusting the amount of shale inhibitor and/or salt in the WSF). As will be appreciated by one of skill in the art, and with the help of this disclosure, the amount of shale inhibitor and/or salt in the WSF may become greater than the target amount of the shale inhibitor and/or salt owing to evaporation of water from the WSF, overtreatment of shale inhibitor and/or salt in the WSF (e.g., adding excess shale inhibitor and/or salt to the WSF), influx of shale inhibitor and/or salt into the WSF, and the like, or combinations thereof.

In aspects where the amount of shale inhibitor and/or salt in the WSF is within about 1%, alternatively within about 5%, alternatively within about 10%, alternatively within about 15%, alternatively within about 20%, or alternatively within about 25% of the target amount of the shale inhibitor and/or the salt, respectively, the WSF may be used in a wellbore servicing operation without further processing (e.g., without adding supplemental shale inhibitor, salt, base fluid, etc., to the WSF). As will be appreciated by one of skill in the art, and with the help of this disclosure, when the amount of shale inhibitor and/or salt in the WSF varies by a relatively small amount (e.g., less than about 1%, alternatively less than about 5%, alternatively less than about 10%) from the target amount of the shale inhibitor and/or the salt, respectively, at least a portion of such variance can be owed to experimental error factors, such as operator error, measuring errors, temperature variation, experimental noise, and the like, or combinations thereof; and in such cases it may not be necessary to adjust the amount of shale inhibitor and/or salt in the WSF.

In an aspect, a method of servicing a wellbore in a subterranean formation can include adjusting the amount of shale inhibitor and/or salt in the WSF to provide for a WSF (e.g., an adjusted WSF, a corrected WSF, a supplemented WSF) having the target amount of the shale inhibitor and/or the salt, respectively.

In aspects where the amount of shale inhibitor and/or salt in the WSF varies by equal to or greater than the threshold amount from the target amount of the shale inhibitor and/or the salt, respectively, the WSF can be adjusted (e.g., contacted with an effective supplemental amount of shale inhibitor, salt, base fluid, etc.) to provide for the WSF having the target amount of the shale inhibitor and/or the salt, respectively.

In an aspect, the effective supplemental amount of can be determined on-the-fly (e.g., in real-time); wherein the WSF having the target amount of the shale inhibitor and/or the salt can be prepared on-location (e.g., on-site; at a wellbore site), by adding the effective supplemental amount of the shale inhibitor, the salt, the base fluid, etc., to the WSF. For purposes of the disclosure herein, the terms "on-the-fly" and "real-time" can be used interchangeably and collectively refer to an action that is performed during an ongoing wellbore servicing operation; wherein performing such action can result in changes to an ongoing wellbore servicing operation on a time scale of less than about 30 minutes, alternatively less than about 15 minutes, alternatively less than about 10 minutes, alternatively less than about 5 minutes, alternatively less than about 1 minute, alternatively less than about 30 seconds, alternatively less than about 15 seconds, alternatively less than about 10 seconds, alternatively less than about 5 seconds, or alternatively less than about 1 second.

For purposes of the disclosure herein, the term "real-time" refers to an action that is performed on a time scale that allows for feedback (e.g., real-time feedback) to an ongoing wellbore servicing operation, wherein the feedback affects the ongoing wellbore servicing operation. For example, real-time data, such as the measured (i.e., actual) amount of shale inhibitor and/or salt in the WSF, can be provided about instantly (e.g., as soon as it is obtained) to a decision factor (e.g., an operator, a computing device), wherein the decision factor can decide or determine whether it is necessary to add the supplemental amount (e.g., of shale inhibitor, salt, base fluid, etc.) to the WSF or not, on a time scale (i.e., about instantly, in real-time) that can affect the ongoing wellbore servicing operation. In some aspects, the computing device can be interfaced or networked with a spectrometer (e.g., colorimeter, portable colorimeter, UV-VIS spectrometer, portable UV-VIS spectrometer). In an aspect, the amount of shale inhibitor and/or salt present in a WSF can be tested on-the-fly during a wellbore servicing operation, and the WSF can be supplemented in real-time such that the wellbore servicing operation does not have to be halted, and thus costly unproductive time can be avoided or minimized.

As will be appreciated by one of skill in the art, and with the help of this disclosure, employing visual detection and/or spectroscopic detection with a portable spectrometer (e.g., portable colorimeter and/or portable UV-VIS spectrometer) of the absorption intensity for the detection solution can generally result in obtaining data regarding the amount of shale inhibitor and/or salt in the WSF in real-time (as opposed to introducing a delay which may be significant by sending a WSF sample to be analyzed in a laboratory setting).

In an aspect, the effective supplemental amount (e.g., of shale inhibitor, salt, base fluid, etc.) can be determined in real-time; wherein the WSF having the target amount of the shale inhibitor and/or the salt, respectively, can be prepared in real-time, by adding the effective supplemental amount (e.g., of supplemental shale inhibitor, salt, base fluid, etc.) to the WSF; and wherein the WSF having the target amount of the shale inhibitor and/or the salt, respectively, may be placed in the wellbore and/or subterranean formation where it may function as intended (e.g., prevent and/or reduce water uptake by water-reactive formations).

In an aspect, a method of servicing a wellbore in a subterranean formation can include (a) preparing a drilling fluid (e.g., including a base fluid, shale inhibitor, and/or a salt, wherein the shale inhibitor and/or the salt is present in the drilling fluid in a target amount (e.g., greater than or equal to 0)); (b) circulating the drilling fluid in the wellbore and/or subterranean formation to yield a circulated drilling fluid; (c) subjecting at least a portion of the circulated drilling fluid to solids removal to yield a substantially solids-free circulated drilling fluid; (d) contacting an aliquot of the solids-free circulated drilling fluid with a detector compound to form a detection solution; wherein the detection solution is characterized by at least one absorption peak wavelength ($\lambda_{max}$) in the range of from about 380 nm to about 760 nm; (e) detecting an absorption intensity for the detection solution at a wavelength within about ±20% of the at least one absorption peak wavelength; (f) comparing the absorption intensity of the detection solution at the wavelength within about ±20% of the at least one absorption peak wavelength with a target absorption intensity of the shale inhibitor and/or the salt to determine the amount of shale inhibitor and/or salt in the circulated drilling fluid; (g) comparing the amount of shale inhibitor and/or salt in the circulated drilling fluid with the target amount of the shale inhibitor and/or salt, wherein the amount of shale inhibitor and/or salt in the circulated drilling fluid varies by equal to or greater than a threshold amount from the target amount of the shale inhibitor and/or salt; (h) responsive to (g), determining an amount of supplemental shale inhibitor and/or salt effective to provide for the circulated drilling fluid having the target amount of the shale inhibitor and/or salt, and contacting the circulated drilling fluid with the effective amount of supplemental shale inhibitor and/or salt on-the-fly; and (i) recycling at least a portion of the circulated drilling fluid to the wellbore and/or subterranean formation. In such aspect, the absorption intensity for the detection solution can be detected visually (e.g., visual detection) and/or with a spectrometer, such as a colorimeter, portable colorimeter, UV-VIS spectrometer, portable UV-VIS spectrometer, etc. (e.g., spectroscopic detection).

In an aspect, a method of servicing a wellbore in a subterranean formation can include (a) preparing a drilling fluid including a base fluid, shale inhibitor, and/or a salt, wherein the shale inhibitor and/or the salt is present in the drilling fluid in a target amount (e.g., a target amount of greater than or equal to zero); (b) circulating the drilling fluid in the wellbore and/or subterranean formation to yield a circulated drilling fluid; (c) subjecting at least a portion of the circulated drilling fluid to solids removal to yield a substantially solids-free circulated drilling fluid; (d) contacting an aliquot of the solids-free circulated drilling fluid with a detector to form a detection solution; wherein the detection solution is characterized by a first absorption peak wavelength (first $\lambda_{max}$) (nm) and optionally by a second absorption peak wavelength (second $\lambda_{max}$); and wherein the detector is contacted with the aliquot of the solids-free circulated drilling fluid in an amount of from about 1 mmol/liter to about 50 mmol/liter detector, based on the total volume of the detection solution; (e) detecting an absorption intensity for the detection solution at a wavelength within about ±20% of the first absorption peak wavelength and optionally the second absorption peak wavelength; (f) comparing the absorption intensity of the detection solution at the wavelength within about ±20% of the first absorption peak wavelength and optionally the second absorption peak wavelength with a target absorption intensity at the wavelength within about ±20% of the first absorption peak wavelength and optionally the second absorption peak wavelength, respectively of the shale inhibitor and/or the salt to determine the amount of shale inhibitor and/or salt in the circulated drilling fluid; (g) comparing the amount of shale inhibitor and/or salt in the circulated drilling fluid with the target amount of the shale inhibitor and/or the salt, wherein the amount of shale inhibitor and/or salt in the circulated drilling fluid varies by equal to or greater than a threshold amount from the target amount of the shale inhibitor and/or the salt; (h) responsive to (g), determining a supplemental amount of shale inhibitor, salt, and/or base fluid effective to provide for the circulated drilling fluid having the target amount of the shale inhibitor and/or the salt, and contacting the circulated drilling fluid with the effective supplemental amount of the shale inhibitor, the salt, and/or the base fluid in real-time; and (i) recycling at least a portion of the circulated drilling fluid to the wellbore and/or subterranean formation. In such aspect, the absorption intensity for the detection solution can be detected visually (e.g., visual detection) and/or with a spectrometer, such as a colorimeter, portable colorimeter, UV-VIS spectrometer, portable UV-VIS spectrometer, etc. (e.g., spectroscopic detection). In aspects where the absorption intensity for the detection solution is detected visually, the color of the detection solution can be purple, blue, or another color. In aspects where the absorption intensity for the detection solution is detected spectroscopically, the detection solution can be subjected to ultraviolet-visible (UV-VIS) spectroscopy and/or colorimetry in a portable UV-VIS spectrometer and/or a portable colorimeter, respectively.

In an aspect, the method of servicing a wellbore in a subterranean formation including detecting a shale inhibitor and/or a salt in a WSF as disclosed herein may display advantages when compared with conventional methods of servicing a wellbore in a subterranean formation. The method of detecting a shale inhibitor and/or a salt in a WSF as disclosed herein may advantageously provide for acquiring real-time data regarding the inhibitory properties of a WSF (e.g., a drilling fluid) with respect to shale formations; which in turn can result in real-time feedback that can allow for correcting the amount of shale inhibitor and/or salt in the WSF. Having the ability to adjust in real-time the amount of shale inhibitor and/or salt in the WSF can advantageously reduce the incidence of non-productive time.

In an aspect, the method of detecting a shale inhibitor and/or a salt in a WSF as disclosed herein may advantageously provide for effectively preventing and/or reducing water uptake by water-reactive formations, which in turn can decrease the risk and/or incidence of adverse events, such as viscosity build-up, bit balling, wellbore caving, wellbore ballooning, subterranean formation integrity loss, collapse of subterranean formation, etc.

In an aspect, the method of detecting a shale inhibitor and/or a salt in a WSF as disclosed herein may advantageously provide for a more cost effective wellbore servicing operation. As will be appreciated by one of skill in the art, and with the help of this disclosure, adding a shale inhibitor and/or a salt to a WSF increases the cost. The ability to accurately determine the concentration of shale inhibitor and/or salt in the WSF could advantageously prevent undue additions of shale inhibitor and/or salt to the WSF, thereby lowering the cost. Additional advantages of the method of servicing a wellbore in a subterranean formation including detecting a shale inhibitor and/or salt in a WSF as disclosed herein may be apparent to one of skill in the art viewing this disclosure.

EXAMPLES

The embodiments having been generally described, the following examples are given as particular embodiments of the disclosure and to demonstrate the practice and advantages thereof. It is understood that the examples are given by way of illustration and are not intended to limit the specification or the claims in any manner.

Example 1

FIG. 1 is a flow chart showing a representative method I for measuring a salt content in a wellbore servicing fluid according to this disclosure. Upon initiating the method I at start 10, method I includes determining a wellbore servicing fluid (e.g., a drilling fluid) water salinity at 20. As noted hereinabove, the wellbore servicing fluid can be a drilling fluid (e.g., a drilling mud). The drilling fluid can be a water based mud (WBM) or an oil based mud (OBM). The water phase salinity of the wellbore servicing fluid can be determined at step 20 via any available methods, such as, without limitation, conductivity, colorimetry, or the like. As step 30, a known volume of the wellbore servicing fluid (e.g., a test sample) is dosed into a container. The known volume of the wellbore servicing fluid can be obtained subsequent circulation of the wellbore servicing fluid downhole (e.g., subsequent passage of a drilling fluid into a drill string in a wellbore, through a drill bit, and back to a surface of the wellbore via an annulus). For example, the known volume of the wellbore servicing fluid can be obtained from a flow line or in a mud pit located at the surface proximate a drilling rig.

As detailed hereinabove, the known volume can include a test sample of the wellbore servicing fluid "as is", or solids can be removed from the known volume of the wellbore servicing fluid and/or the known volume of the wellbore servicing fluid can be diluted to provide the test sample. For example, as indicated at step 40, method I can further include adding a known amount of diluent (e.g., water) to the known volume of wellbore servicing fluid and optionally mixing to provide the test sample. Without intending to be limited by theory, diluting the known volume may aid in dispersing and/or separating any solids remaining in the known volume of the wellbore servicing fluid to aid in obtaining a substantially solids-free test sample. For example, step 40 can include centrifuging the known volume of wellbore servicing fluid to form a solids/bottom layer and an upper/supernatant liquid layer, taking an amount from the supernatant (e.g., the water phase of the WSF), and diluting the amount of supernatant with water (optionally with mixing) to provide the test sample. Method I includes at step 50, adding a detector compound such as a chromophore dye to the test sample and mixing. Method I further includes at step 60A, measuring the salt content of the test sample utilizing the colorimetric method detailed herein. Method I further includes, at step 70, reporting the data from step 60A to a computer control system. At step 80A, method I includes, determining (e.g., via the control system) a wellbore servicing fluid (e.g., drilling fluid) treatment based on water phase salinity (WPS) and optionally other shale inhibitors. Method I includes, at step 90A, subjecting the wellbore servicing fluid of the wellbore servicing system to the treatment, for example by adding salt or water to the wellbore servicing fluid system (e.g., to the mud pit). At step 100, method I can include waiting for a next time interval to test the wellbore servicing fluid system (e.g., the mud system). The waiting time at step 100 can depend, for example and without limitation, on the wellbore servicing fluid system volume (e.g., the mud system volume) and pump rate. At 110, the method includes initiating the method again by returning to start 10.

Example 2

Figure 2:
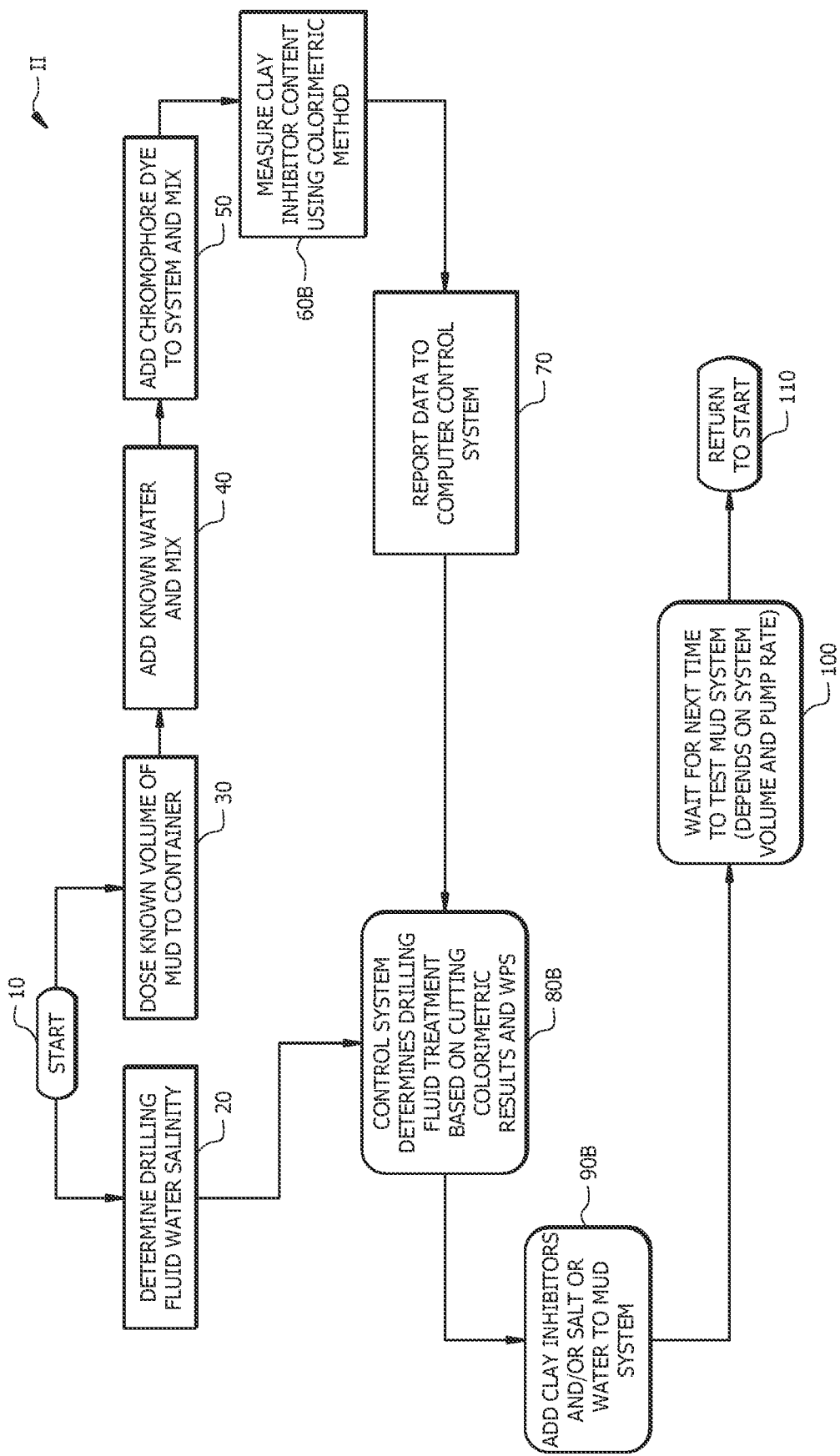
FIG. 2 is a flow chart showing a representative method for measuring a shale inhibitor content in a wellbore servicing fluid according to this disclosure.

FIG. 2 is a flow chart showing a representative method II for measuring a shale inhibitor content in a wellbore servicing fluid according to this disclosure. Upon initiating the method II at start 10, method II includes determining a wellbore servicing fluid (e.g., a drilling fluid) water salinity at 20 and dosing a known volume of the wellbore servicing fluid into a container. As noted hereinabove, the wellbore servicing fluid can be a drilling fluid (e.g., a drilling mud). The drilling fluid can be a water based mud (WBM) or an oil based mud (OBM). The water phase salinity of the wellbore servicing fluid can be determined at step 20 via any available methods, such as, without limitation, conductivity, colorimetry, or the like. As noted hereinabove, the known volume of the wellbore servicing fluid dosed at step 30 can be obtained subsequent circulation of the wellbore servicing fluid downhole (e.g., subsequent passage of a drilling fluid into a drill string in a wellbore, through a drill bit, and back to a surface of the wellbore via an annulus). For example, the known volume of the wellbore servicing fluid can be obtained from a flow line or in a mud pit uphole. As detailed hereinabove with reference to FIG. 1, the known volume can include a test sample "as is", or solids can be removed from the known volume of the wellbore servicing fluid and/or the known volume of the wellbore servicing fluid can be diluted to provide a test sample. For example, as indicated at step 40, method II can further include adding a known amount of diluent (e.g., water) to the known volume of wellbore servicing fluid and optionally mixing to provide the test sample. Step 40 can include, for example, centrifuging the known volume of wellbore servicing fluid, taking an amount from the supernatant (e.g., the water phase of the WSF), and diluting with water (with optional mixing) to provide the test sample. Method II includes at step 50, adding a detector compound such as a chromophore dye to the test sample and mixing. Method II further includes at step 60B, measuring the shale inhibitor content of the test sample utilizing the colorimetric method detailed herein. Method II further includes, at step 70, reporting the data from step 60B to a computer control system. At step 80B, method II includes, determining (e.g., via the control system) wellbore servicing fluid (e.g., drilling fluid) treatment based on the colorimetric results from step 60B and water phase salinity (WPS) from step 20. Method II includes, at step 90B, subjecting the wellbore servicing fluid of the wellbore servicing system to the treatment, for example by adding shale inhibitor(s) and/or salt(s) to the wellbore servicing fluid system (e.g., to the mud pit). At step 100, method II includes waiting for a next time interval to test the wellbore servicing fluid system (e.g., the mud system). The waiting time at step 100 can depend, for example and without limitation, on the wellbore servicing fluid system volume (e.g., the mud system volume) and pump rate. At 110, the method II includes initiating the method again by returning to start 10. Steps 10, 20, 30, 40, 50, 70, 100, and 110 can be substantially the same for method II as for method I of FIG. 1.

ADDITIONAL DISCLOSURE

A first aspect, which is a method of detecting a shale inhibitor and/or a salt in a wellbore servicing fluid (WSF) comprising: (a) contacting an aliquot of the WSF with a detector compound to form a detection solution; wherein the detection solution is characterized by at least one absorption peak wavelength, for example in the range of from about 380 nanometers (nm) to about 760 nm; (b) detecting an absorption intensity for the detection solution at a wavelength within about ±20% of the at least one absorption peak wavelength; (c) comparing the absorption intensity of the detection solution at the wavelength within about ±20% of the at least one absorption peak wavelength with a target absorption intensity of the shale inhibitor and/or the salt to determine the amount of shale inhibitor and/or salt in the WSF; and (d) comparing the amount of shale inhibitor and/or salt in the WSF with a target amount of the shale inhibitor and/or the salt.

A second aspect, which is the method of the first aspect, wherein the detection solution is characterized by a visible color.

A third aspect, which is the method of the second aspect, wherein the aliquot of the WSF is further characterized by a visible color, and wherein the visible color and/or color intensity of the detection solution is different from the visible color and/or color intensity of the aliquot of the WSF.

A fourth aspect, which is the method of any one of the first through the third aspects, wherein (b) detecting an absorption intensity for the detection solution at a wavelength within about ±20% of the at least one absorption peak wavelength further comprises subjecting at least a portion of the detection solution to ultraviolet-visible (UV-VIS) spectroscopy and/or colorimetry to yield the absorption intensity of the detection solution at the wavelength within about ±20% of the at least one absorption peak wavelength.

A fifth aspect, which is the method of the fourth aspect, wherein at least a portion of the detection solution is analyzed in a portable UV-VIS spectrometer and/or a portable colorimeter.

A sixth aspect, which is the method of any one of the first through the fifth aspects, wherein (c) comparing the absorption intensity of the detection solution at the wavelength within about ±20% of the at least one absorption peak wavelength with a target absorption intensity of the shale inhibitor and/or the salt comprises optically comparing the color and/or color intensity of the detection solution with a target color and/or color intensity, respectively.

A seventh aspect, which is the method of the sixth aspect, wherein determining the amount of shale inhibitor and/or salt in the WSF further comprises using a calibration curve that correlates absorption intensity at the wavelength within about ±20% of the at least one absorption peak wavelength with the amount of the shale inhibitor and/or the salt, respectively.

An eighth aspect, which is the method of any one of the first through the seventh aspects, wherein determining the amount of shale inhibitor and/or salt in the WSF further comprises visually comparing a visually observed color and/or color intensity of the detection solution with a reference color chart that correlates color and/or color intensity, respectively, with the amount of the shale inhibitor and/or the salt, respectively.

A ninth aspect, which is the method of any one of the first through the eighth aspects, wherein the amount of shale inhibitor and/or salt in the WSF varies by less than a threshold amount from the target amount of the shale inhibitor and/or the salt, respectively, and wherein at least a portion of the WSF is placed in a wellbore and/or subterranean formation.

A tenth aspect, which is the method of the ninth aspect, wherein the WSF is placed in a wellbore and/or subterranean formation prior to determining the amount of shale inhibitor and/or salt in the WSF.

An eleventh aspect, which is the method of any one of the first through the ninth aspects, wherein the WSF is placed in a wellbore and/or subterranean formation subsequent to determining the amount of shale inhibitor and/or salt in the WSF.

A twelfth aspect, which is the method of any one of the first through the eighth aspects, wherein the amount of shale inhibitor and/or salt in the WSF varies by equal to or greater than a threshold amount from the target amount of the shale inhibitor and/or the salt, and wherein the WSF is contacted with an effective supplemental amount of shale inhibitor, salt, and/or base fluid to provide for the WSF having the target amount of the shale inhibitor and/or the salt.

A thirteenth aspect, which is the method of the twelfth aspect further comprising determining the effective supplemental amount and preparing the WSF having the target amount of the shale inhibitor and/or the salt on-the-fly.

A fourteenth aspect, which is the method of any one of the twelfth and the thirteenth aspects further comprising placing at least a portion of the WSF having the target amount of the shale and/or the salt inhibitor in a wellbore and/or subterranean formation.

A fifteenth aspect, which is the method of any one of the first through the fourteenth aspects, wherein the WSF is recovered from a wellbore and/or subterranean formation, wherein at least a portion of the recovered WSF is subjected to a solids removal procedure to yield a substantially solids-free WSF, and wherein an aliquot of the substantially solids-free WSF is contacted with a detector compound to form the detection solution in (a).

A sixteenth aspect, which is the method of the fifteenth aspect, wherein the solids removal procedure is selected from the group consisting of filtration, sedimentation, decantation, centrifugation, screening, chemical dissolution, combinations thereof A seventeenth aspect, which is the method of any one of the first through the sixteenth aspects further comprising heating the detection solution prior to (b) detecting an absorption intensity for the detection solution at a wavelength within about ±20% of the at least one absorption peak wavelength.

An eighteenth aspect, which is the method of any one of the first through the seventeenth aspects, wherein the detector compound comprises methylene blue, ninhydrin, indane-1,2,3-trione, hydrantin, quinhydrone, Dragendorff reagent, chloranil, N-halosuccinimide, N-bromosuccinimide, N-iodosuccinimide, a hydrazo compound, a diazonium salt, fluorescein, fluorescein halide, fluorescein chloride, or combinations thereof; additionally or alternatively, the detector compound may be a chromophore.

A nineteenth aspect, which is the method of any one of the first through the eighteenth aspects, wherein the shale inhibitor comprises a salt, a polymer, a charged polymer, a primary amine functional group, a protonated primary amine functional group, a secondary amine functional group, a protonated secondary amine functional group, a tertiary amine functional group, a protonated tertiary amine functional group, or a combination thereof.

A twentieth aspect, which is the method of any one of the first through the nineteenth aspects, wherein the WSF comprises a drilling fluid.

A twenty-first aspect, which is a method of servicing a wellbore in a subterranean formation comprising (a) preparing a drilling fluid comprising a base fluid. a shale inhibitor, and/or a salt, wherein the shale inhibitor and/or the salt are present in the drilling fluid in a target amount, which is greater than or equal to zero; (b) circulating the drilling fluid in the wellbore and/or subterranean formation to yield a circulated drilling fluid; (c) subjecting at least a portion of the circulated drilling fluid to solids removal to yield a substantially solids-free circulated drilling fluid; (d) contacting an aliquot of the solids-free circulated drilling fluid with a detector compound to form a detection solution; wherein the detection solution is characterized by at least one absorption peak wavelength in the range of from about 380 nanometers (nm) to about 760 nm; (e) detecting an absorption intensity for the detection solution at a wavelength within about ±20% of the at least one absorption peak wavelength; (f) comparing the absorption intensity of the detection solution at the wavelength within about ±20% of the at least one absorption peak wavelength with a target absorption intensity of the shale inhibitor and/or the salt to determine the amount of shale inhibitor and/or the salt, respectively, in the circulated drilling fluid; and (g) comparing the amount of shale inhibitor and/or salt in the circulated drilling fluid with the target amount of the shale inhibitor and/or the salt, respectively.

A twenty-second aspect, which is the method of the twenty-first aspect, wherein the detection solution is characterized by a visible color.

A twenty-third aspect, which is the method of the twenty-second aspect, wherein the aliquot of the WSF is further characterized by a visible color, and wherein the visible color and/or color intensity of the detection solution is different from the visible color and/or color intensity of the aliquot of the WSF.

A twenty-fourth aspect, which is the method of any one of the twenty-first through the twenty-third aspects, wherein the amount of shale inhibitor and/or salt in the circulated drilling fluid varies by less than a threshold amount from the target amount of the shale inhibitor and/or the salt, respectively; and wherein at least a portion of the circulated drilling fluid is recycled to the wellbore and/or subterranean formation.

A twenty-fifth aspect, which is the method of any one of the twenty-first through the twenty-third aspects, wherein the amount of shale inhibitor and/or salt in the circulated drilling fluid varies by equal to or greater than a threshold amount from the target amount of the shale inhibitor and/or the salt, respectively; wherein the circulated drilling fluid is contacted with an effective supplemental amount of shale inhibitor, salt, and/or base fluid to provide for the circulated drilling fluid having the target amount of the shale inhibitor and/or the salt; and wherein at least a portion of the circulated drilling fluid is recycled to the wellbore and/or subterranean formation.

A twenty-sixth aspect, which is the method of the twenty-fifth aspect further comprising determining the effective supplemental amount of shale inhibitor, salt, and/or base fluid in real-time and preparing the circulated drilling fluid having the target amount of the shale inhibitor and/or the salt, respectively, on-the-fly.

A twenty-seventh aspect, which is a method of servicing a wellbore in a subterranean formation comprising (a) preparing a drilling fluid comprising a base fluid, a shale inhibitor, and/or a salt, wherein the shale inhibitor and/or the salt are present in the drilling fluid in a target amount; (b) circulating the drilling fluid in the wellbore and/or subterranean formation to yield a circulated drilling fluid; (c) subjecting at least a portion of the circulated drilling fluid to solids removal to yield a substantially solids-free circulated drilling fluid; (d) contacting an aliquot of the solids-free circulated drilling fluid with a detector compound to form a detection solution; wherein the detection solution is characterized by a first absorption peak wavelength and optionally by a second absorption peak wavelength; and wherein the detector compound is optionally contacted with the aliquot of the solids-free circulated drilling fluid in an amount of from about 0.01 mmol/liter to about 200 mmol/liter detector compound, based on the total volume of the detection solution; (e) detecting an absorption intensity for the detection solution at a wavelength within about ±20% of the first absorption peak wavelength and optionally the second absorption peak wavelength; (f) comparing the absorption intensity of the detection solution at the wavelength within about ±20% of the first absorption peak wavelength and optionally a second absorption peak wavelength with a target absorption intensity at the wavelength within about ±20% of the first absorption peak wavelength and optionally the second absorption peak wavelength, respectively, of the shale inhibitor and/or the salt to determine the amount of shale inhibitor and/or salt in the circulated drilling fluid; and (g) comparing the amount of shale inhibitor and/or salt in the circulated drilling fluid with the target amount of the shale inhibitor and/or the salt, respectively.

A twenty-eighth aspect, which is the method of the twenty-seventh aspect, wherein the detection solution is characterized by a visible color.

A twenty-ninth aspect, which is the method of the twenty-eighth aspect, wherein the aliquot of the WSF is further characterized by a visible color, and wherein the visible color and/or color intensity of the detection solution is different from the visible color and/or color intensity of the aliquot of the WSF.

A thirtieth aspect, which is the method of any one of the twenty-seventh through the twenty-ninth aspects, wherein (f) comparing the absorption intensity of the detection solution at the wavelength within about ±20% of the first absorption peak wavelength and optionally the second absorption peak wavelength with a target absorption intensity of the shale inhibitor and/or the salt comprises optically comparing the color and/or color intensity of the detection solution with a target color and/or color intensity, respectively.

A thirty-first aspect, which is the method of any one of the twenty-seventh through the thirtieth aspects, wherein (f) comparing the absorption intensity of the detection solution at the wavelength within about ±20% of the first absorption peak wavelength and optionally the second absorption peak wavelength with a target absorption intensity of the shale inhibitor and/or the salt further comprises subjecting at least a portion of the detection solution to ultraviolet-visible (UV-VIS) spectroscopy and/or colorimetry in a portable UV-VIS spectrometer and/or a portable colorimeter, respectively, to yield the absorption intensity of the detection solution at the wavelength within about ±20% of the first absorption peak wavelength and optionally the second absorption peak wavelength.

A thirty-second aspect, which is the method of any one of the twenty-seventh through the thirty-first aspects, wherein the amount of shale inhibitor and/or salt in the circulated drilling fluid varies by equal to or greater than a threshold amount from the target amount of the shale inhibitor and/or the salt, respectively; wherein the circulated drilling fluid is contacted with an effective supplemental amount of shale inhibitor, salt, and/or base fluid to provide for the circulated drilling fluid having the target amount of the shale inhibitor and/or the salt; and wherein at least a portion of the circulated drilling fluid is recycled to the wellbore and/or subterranean formation.

A thirty-third aspect, which is the method of the thirty-second aspect further comprising determining the effective supplemental amount of shale inhibitor, salt, and/or base fluid and preparing the circulated drilling fluid having the target amount of the shale inhibitor and/or the salt, respectively, in real-time.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$, and an upper limit, $R_U$, is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

For purposes of the disclosure herein, the term "comprising" includes "consisting" or "consisting essentially of." Further, for purposes of the disclosure herein, the term "including" includes "comprising," "consisting," or "consisting essentially of."

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A method of detecting a salt content of a wellbore servicing fluid (WSF) of a wellbore servicing fluid system as described herein, the method comprising:
  (a) determining a water salinity of a wellbore servicing fluid;
  (b) dosing an aliquot of the wellbore servicing fluid into a container;
  (c) combining the aliquot of the wellbore servicing fluid with a detector compound specific to the salt and mixing to provide a detection solution in the container, wherein the detection solution is characterized by at least one absorption peak wavelength in the range of from about 380 nanometers (nm) to about 760 nm;
  (d) measuring the salt content of the detection solution using colorimetry by detecting an absorption intensity for the detection solution at a wavelength within about ±20% of the at least one absorption peak wavelength, comparing the absorption intensity of the detection solution at the wavelength within about ±20% of the at least one absorption peak wavelength with a target absorption intensity to determine the amount of salt in the WSF, and comparing the amount of salt in the WSF with a target amount of the salt;

(e) reporting the data from the measuring at (d) to a computer control system;

(f) determining a wellbore servicing fluid treatment based on the salt content and/or a content of shale inhibitors; and (g) subjecting the wellbore servicing fluid of the wellbore servicing fluid system to the treatment.

2. The method of claim 1 further comprising:
adding a known volume of diluent and mixing prior to (c); and/or (h) waiting for a waiting time to retest the wellbore servicing fluid system; and (i) repeating steps (a) through (g) after the waiting time.

3. The method of claim 1, wherein the wellbore servicing fluid comprises a drilling fluid.

4. The method of claim 3, wherein the drilling fluid has been recovered from circulation downhole.

5. The method of claim 3, wherein the wellbore servicing fluid comprises a water based mud (WBM).

6. The method of claim 3, wherein the wellbore servicing fluid comprises an oil based mud (OBM), and wherein dosing at (b) further comprises separating an aqueous phase from an oil phase, and wherein the aliquot comprises at least a portion of the separated aqueous phase.

7. The method of claim 1, wherein (d) measuring the salt content using colorimetry at (e) comprises utilizing an analyzer comprising photosensitive dye(s) comprising the chromophore specific to the salt.

8. The method of claim 1, wherein the salt comprises NaCl, KCl, NaBr, $CaCl_2$, $CaBr_2$, $MgCl_2$, $MgBr_2$, $ZnBr_2$, an acetate salt, sodium acetate, potassium acetate, ammonium chloride ($NH_4Cl$), potassium phosphate, sodium formate, potassium formate, cesium formate, or a combination thereof.

9. The method of claim 8, wherein the wellbore servicing fluid comprises a brine.

10. The method of claim 1, wherein the aliquot of the wellbore servicing fluid comprises a solids reduced and/or diluted volume of the wellbore servicing fluid.

11. A method of detecting a shale inhibitor content of a wellbore servicing fluid (WSF) of a wellbore servicing fluid system as described herein, the method comprising:

(a) determining a water phase salinity (WPS) of a wellbore servicing fluid;

(b) dosing an aliquot of the wellbore servicing fluid into a container;

(c) combining the aliquot of the wellbore servicing fluid with a detector compound specific to the shale inhibitor and mixing to provide a detection solution in the container, wherein the detection solution is characterized by at least one absorption peak wavelength in the range of from about 380 nanometers (nm) to about 760 nm;

(d) measuring the shale inhibitor content of the detection solution using colorimetry by detecting an absorption intensity for the detection solution at a wavelength within about ±20% of the at least one absorption peak wavelength, comparing the absorption intensity of the detection solution at the wavelength within about ±20% of the at least one absorption peak wavelength with a target absorption intensity to determine the amount of shale inhibitor in the WSF, and comparing the amount of shale inhibitor in the WSF with a target amount of the shale inhibitor;

(e) reporting the data from the measuring at (d) to a computer control system;

(f) determining a wellbore servicing fluid treatment based on the water phase salinity (WPS) from (a) and the content of shale inhibitor from (d); and (g) subjecting the wellbore servicing fluid of the wellbore servicing fluid system to the treatment.

12. The method of claim 11 further comprising:
adding a known volume of diluent and mixing prior to (c); and/or (h) waiting for a waiting time to retest the wellbore servicing fluid system; and (i) repeating steps (a) through (g) after the waiting time.

13. The method of claim 11, wherein the wellbore servicing fluid comprises a drilling fluid.

14. The method of claim 13, wherein the drilling fluid has been recovered from circulation downhole.

15. The method of claim 13, wherein the wellbore servicing fluid comprises a water based mud (WBM).

16. The method of claim 13, wherein the wellbore servicing fluid comprises an oil based mud (OBM), and wherein dosing at (b) further comprises separating an aqueous phase from an oil phase, and wherein the aliquot comprises at least a portion of the separated aqueous phase.

17. The method of claim 11, wherein (d) measuring the shale inhibitor content of the detection solution using colorimetry at (d) comprises utilizing an analyzer comprising photosensitive dye(s) comprising the chromophore specific to the shale inhibitor.

18. The method of claim 11, wherein the shale inhibitor comprises a polymer, a charged polymer, a salt, or a combination thereof.

19. The method of claim 18, wherein the shale inhibitor comprises a high molecular weight polymer, potassium chloride, sodium chloride, or a combination thereof.

20. The method of claim 11, wherein the aliquot of the wellbore servicing fluid comprises a solids reduced and/or diluted volume of the wellbore servicing fluid.

* * * * *